United States Patent
Takayanagi et al.

(10) Patent No.: US 10,751,546 B2
(45) Date of Patent: Aug. 25, 2020

(54) RADIATION TREATMENT PLANNING SYSTEM AND RADIATION TREATMENT SYSTEM

(71) Applicants: Hitachi, Ltd., Tokyo (JP); NATIONAL UNIVERSITY CORPORATION HOKKAIDO UNIVERSITY, Sapporo-shi, Hokkaido (JP)

(72) Inventors: Taisuke Takayanagi, Tokyo (JP); Toru Umekawa, Tokyo (JP); Shinichiro Fujitaka, Tokyo (JP); Seishin Takao, Sapporo (JP)

(73) Assignees: HITACHI, LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 287 days.

(21) Appl. No.: 15/805,566

(22) Filed: Nov. 7, 2017

(65) Prior Publication Data

US 2018/0126188 A1 May 10, 2018

(30) Foreign Application Priority Data

Nov. 8, 2016 (JP) ................. 2016-218383

(51) Int. Cl.
    *A61N 5/10* (2006.01)
(52) U.S. Cl.
    CPC ......... *A61N 5/1031* (2013.01); *A61N 5/1038* (2013.01); *A61N 2005/1087* (2013.01)
(58) Field of Classification Search
    CPC .... A61N 5/103–1039; A61N 2005/1032–1041
    See application file for complete search history.

(56) References Cited

U.S. PATENT DOCUMENTS

| 2008/0317204 | A1* | 12/2008 | Sunnanaweera | A61N 5/1049 378/65 |
| 2011/0153547 | A1* | 6/2011 | McNutt | G06F 19/3481 706/54 |
| 2017/0083682 | A1* | 3/2017 | McNutt | G16H 50/30 |
| 2017/0259083 | A1* | 9/2017 | Nakatsugawa | A61B 6/032 |
| 2018/0099151 | A1* | 4/2018 | Sullivan | A61B 6/032 |

OTHER PUBLICATIONS

Lindsey M. Appenzoller, et al., "Predicting dose-volume histograms for organs-at-risk in IMRT planning", Medical Physics 39 (12), Dec. 2012 pp. 7446-7461.

* cited by examiner

*Primary Examiner* — Catherine B Kuhlman
(74) *Attorney, Agent, or Firm* — Mattingly & Malur, PC

(57) ABSTRACT

Provided are a radiation treatment planning system and a radiation treatment system that are capable of achieving time shortening and labor saving of treatment planning making when a radiation treatment is planned. A predicted DVH calculation portion 4034 of an arithmetic processing device 403 in a radiation treatment planning system 400 anisotropically enlarges a target region 501 in an irradiated body image which is input to the radiation treatment planning system 400, and calculates an overlap volume OV with an organ-at-risk region 502 per the number of times of enlargement. A DVH (Dose Volume Histogram) is predicted from a volume of the calculated OV, and a dose histogram in the OV per the number of times of enlargement which is calculated from a past treatment planning data group, and is displayed on a display device 401.

8 Claims, 7 Drawing Sheets

RADIATION TREATMENT PLANNING SYSTEM AND RADIATION TREATMENT SYSTEM

TECHNICAL FIELD

The present invention relates to a radiation treatment planning system and a radiation treatment system.

BACKGROUND ART

For the purpose of shortening the time required for treatment planning and for reducing the labor of required for treatment planning making, in NPL 1, a technology of predicting a dose volume histogram (DVH) is implemented when a particular irradiation is carried out based on a positional relationship between a target and an organ-at-risk, and a past treatment planning data group. The operator is assisted in the treatment planning by indicating the DVH as a target value in an intensity modulated radiotherapy (IMRT) treatment.

CITATION LIST

Patent Literature

NPL 1: Lindsey M. Appenzoller, et al., "Predicting dose-volume histograms for organs-at-risk in IMRT planning", Med. Phys. 39 (12), December (2012) 7446-7461

SUMMARY OF INVENTION

Technical Problem

In the treatment using the radiation, a demand for a particle therapy system using a particle beam (referred to as a charged particle beam) that is represented by a proton beam or a carbon beam having high dose conformity to a tumor cell which becomes the target has been increased.

Even in the particle therapy system, there is a need to perform the irradiation of the designated dose to concentrate on the tumor region as accurately as possible, and to reduce the dose of other normal tissues as much as possible. In the particle beam therapy, as a method for concentrating the dose, a use of a scanning method is spread out. This is a method for performing the irradiation to fill an inside of the tumor by guiding the minute particle beam to an arbitrary position in a plane, and applying the high dose only to the tumor region.

A radiation treatment planning system is a system that simulates dose distribution in a patient body by numerical calculation, based on information in the patient body which is obtained from a CT image or the like. The operator determines irradiation conditions such as an irradiation direction of the particle beam, beam energy, an irradiation point, or an irradiation amount while referring to a calculation result of the radiation treatment planning system. Hereinafter, a general process thereof will be simply described. In the scanning irradiation, there is a spot scanning method or a raster method, but here, the description thereof will be made on the premise of the spot scanning method.

First, the operator inputs a target region to be irradiated with the radiation. In most cases, the position of the organ-at-risk to be avoided as much as possible from the irradiation with the radiation is also input in the same manner, and is registered.

Next, the operator sets a dose value (prescription dose) to be a target with respect to each of the registered regions. In the prescription dose, for example, there is a case where the dose of 60 Gy is applied to 95% or more of a volume in the target, or a case where the dose of 30 Gy or more is not applied to 60% or more of the volume in the organ-at-risk.

Subsequently, the operator determines the most suitable irradiation condition that satisfies the set prescription dose. For example, the suitable irradiation condition is a condition where the maximum dose is applied to the target in a scope in which a trouble is not generated in the organ-at-risk.

In the determining of the irradiation condition, an objective function which is obtained by quantifying a deviation from the prescription dose is used. It is known that there is a trade-off relationship between the applied dose to the target and the dose reduction of the organ-at-risk, and the objective function of the organ-at-risk is worsened if the objective function of the target is improved. Therefore, the operator has a need to operate the radiation treatment planning system by adjusting and repeating input parameters relating to the optimization of the irradiation condition, and searching for the most suitable irradiation condition.

In the radiation treatment planning system of the related art which is necessary for such a repeated operation, there is a problem that time of the planning making is prolonged in a case (for example, head and neck portion) where a large number of organs-at-risk exist in the vicinity of the target.

There is also a problem that results of the treatment planning vary depending on the amount of experiences of the operator, or the like. For example, in a case where a distance from the target to the organ-at-risk is relatively distant, it is possible to improve the respective objective functions at the same time. However, depending on the operator, it is considered that the case is in the same manner as a case where the target and the organ-at-risk are adjacent to each other (it is not possible to improve the objective functions of the target and the organ-at-risk at the same time), and regardless of existence of the more suitable irradiation condition, the operator may make an oversight of the existence of the suitable irradiation condition by determining that the suitable irradiation condition does not exist above the made treatment plan.

In this manner, even in the radiation treatment of the scanning irradiation method, the radiation treatment planning system which is capable of achieving time shortening and labor saving of the treatment planning making is desired.

On the contrary, it is conceivable to apply the method of NPL 1 described above. However, there is a possibility that it is not possible to accurately predict DVH with respect to the radiation treatment of the scanning irradiation method, and it is not possible to realize the time shortening and the labor saving of the treatment planning making.

This is because NPL 1 is a technology of predicting the DVH based on a case where the dose distribution of IMRT is isotropically spread out in the vicinity of the target, and in the scanning irradiation or the like, it is clear that there is room for further improvement of prediction accuracy of the DVH by studies of inventors of the present invention. Specifically, in the radiation treatment of the scanning irradiation method, by existence of the Bragg peak and a difference of a spot diameter per energy, the dose distribution has the anisotropic spread depending on an irradiation angle of the beam, a depth from a body surface to the target, or the like. Therefore, it is clear that it is possible to improve the prediction accuracy of the DVH by reflecting the anisotropic spread and predicting the DVH, by the studies of the inventors of the present invention.

An object of the present invention is to provide a radiation treatment planning system and a radiation treatment system which are capable of achieving time shortening and labor saving of treatment planning making when a radiation treatment is planned.

Solution to Problem

In order to solve the above problems, for example, a configuration written in the scope of the claims is adopted. The present invention includes a plurality of means for solving the above problems, but as an example thereof, there is provided a radiation treatment planning system for preparing treatment planning by radiation, the system including a database that stores past treatment planning data, a display device that displays a DVH, and a predicted DVH calculation portion that calculates a predicted DVH, in which the predicted DVH calculation portion calculates an overlap volume (OV) between an organ-at-risk region and a target region by anisotropically changing the target region in an image where an irradiated body is imaged, and calculates the predicted DVH based on the calculated OV, and the past treatment planning data which is stored in the database, and the display device displays the predicted DVH which is calculated by the predicted DVH calculation portion.

Advantageous Effects of Invention

According to the present invention, it is possible to achieve time shortening and labor saving of treatment planning making when a radiation treatment is planned.

DESCRIPTION OF EMBODIMENTS

Embodiments of a radiation treatment planning system and a radiation treatment system of the present invention will be described by using FIGS. 1 to 7. An embodiment of the present invention is the radiation treatment system that performs a radiation treatment (particle beam therapy) by a scanning irradiation method, and the radiation treatment planning system that makes treatment planning thereof.

Figure 1:
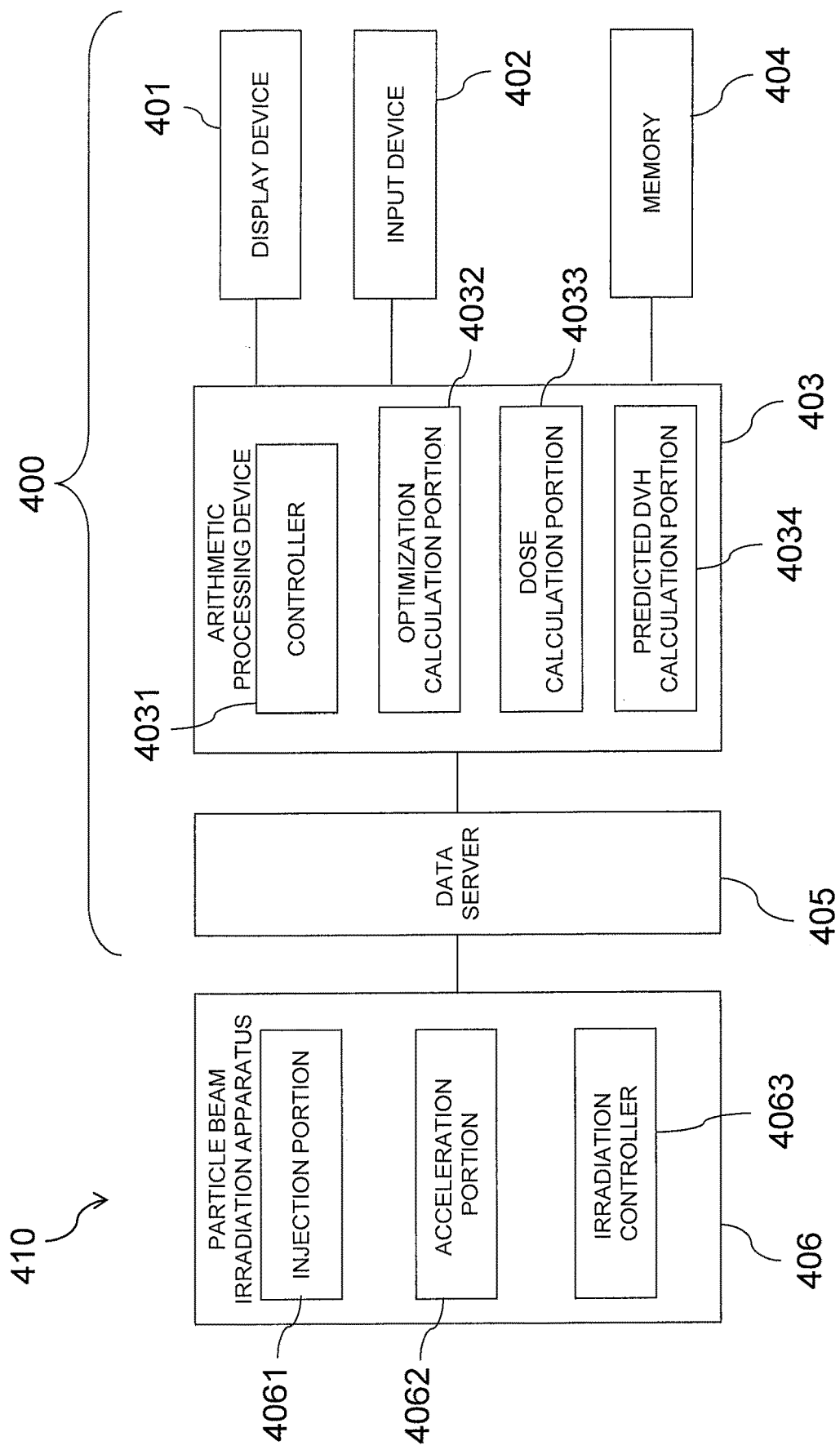
FIG. 1 is a diagram illustrating of a whole configuration of a particle beam therapy system of the present invention.
Figure 2:
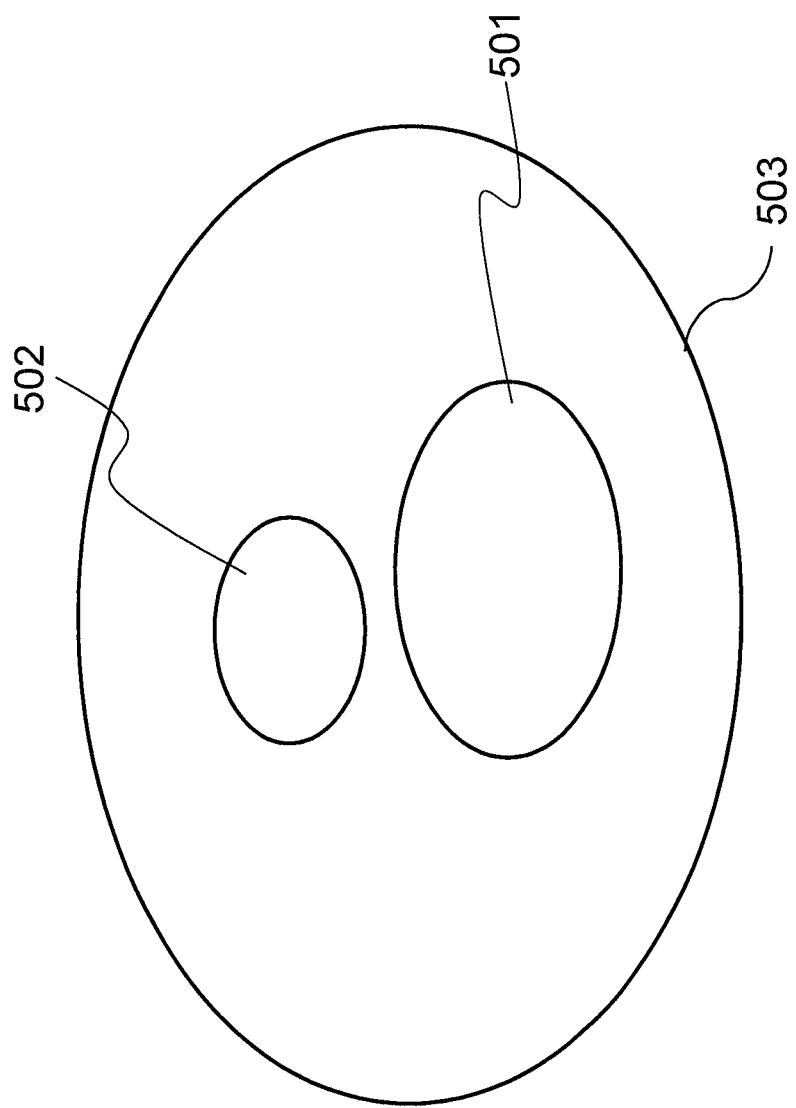
FIG. 2 is a diagram illustrating a screen of a target region or the like on a CT screen in a radiation treatment planning system of the present invention.
Figure 3:
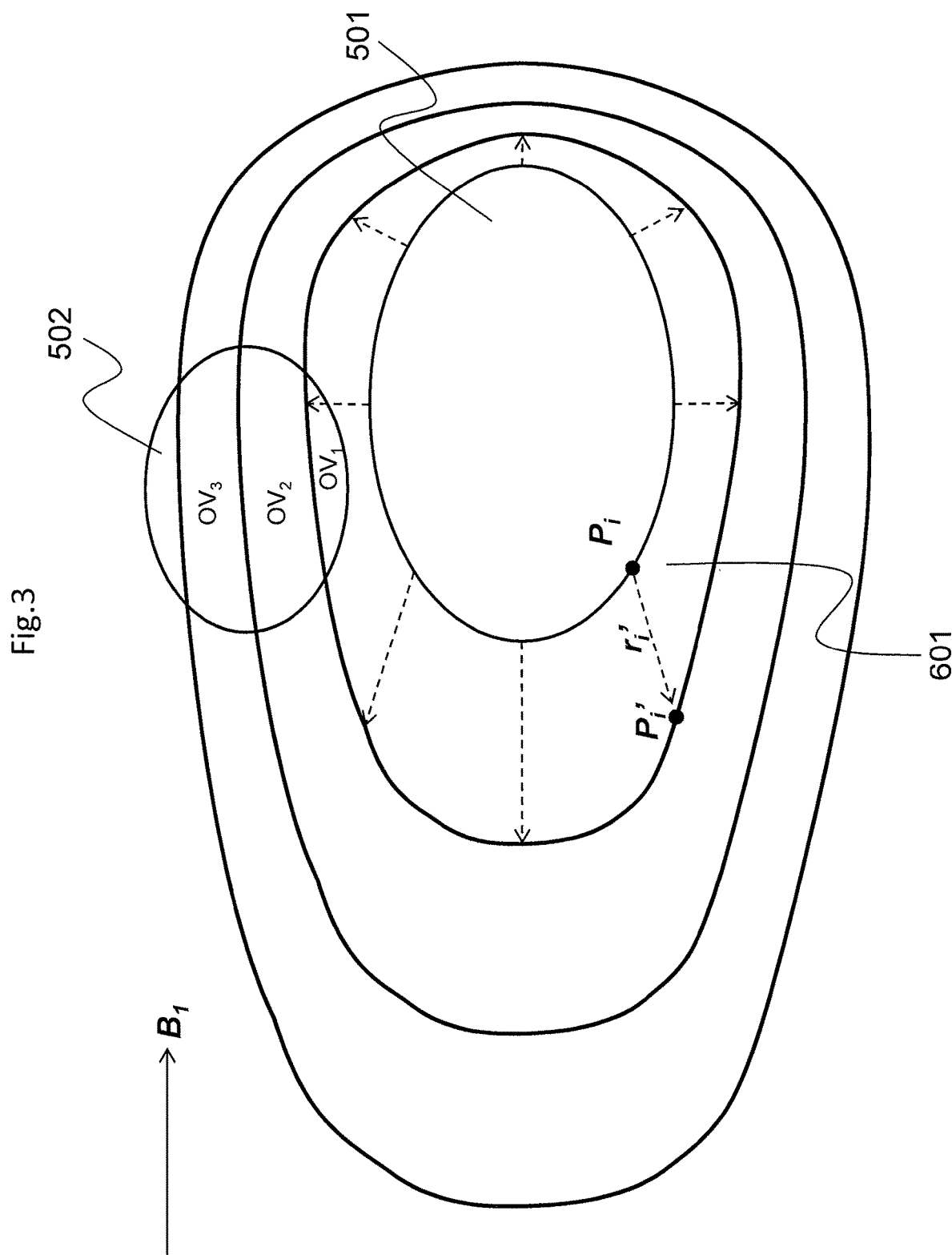
FIG. 3 is a diagram for describing calculation processing of an OV and a predicted DVH in the radiation treatment planning system of the present invention.
Figure 4:
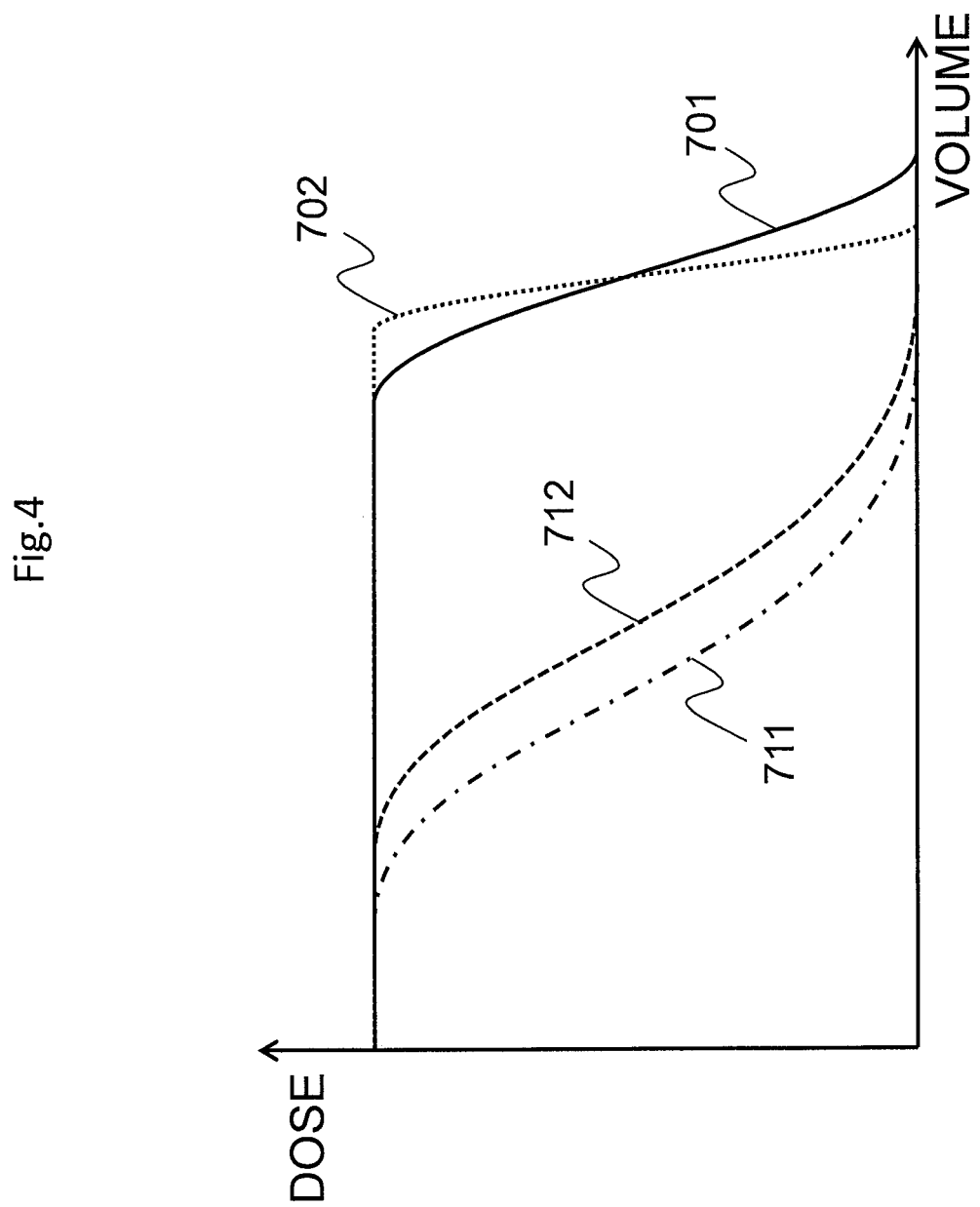
FIG. 4 is a diagram for describing an example of a screen on which the predicted DVH and the calculated DVH are displayed in the radiation treatment planning system of the present invention.
Figure 5:
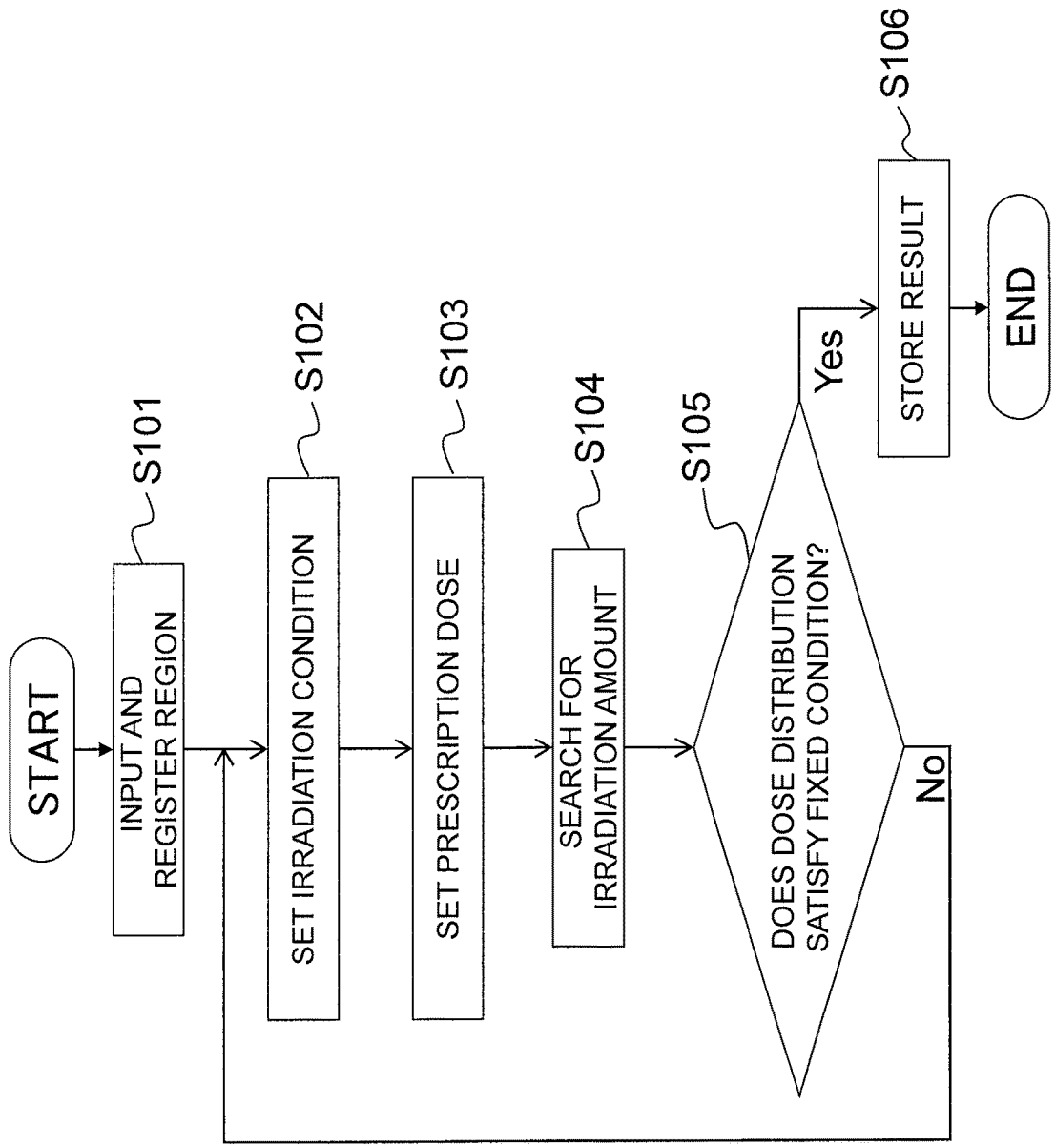
FIG. 5 is a diagram representing a flow of a processing operation for making treatment planning in the radiation treatment planning system.
Figure 6:
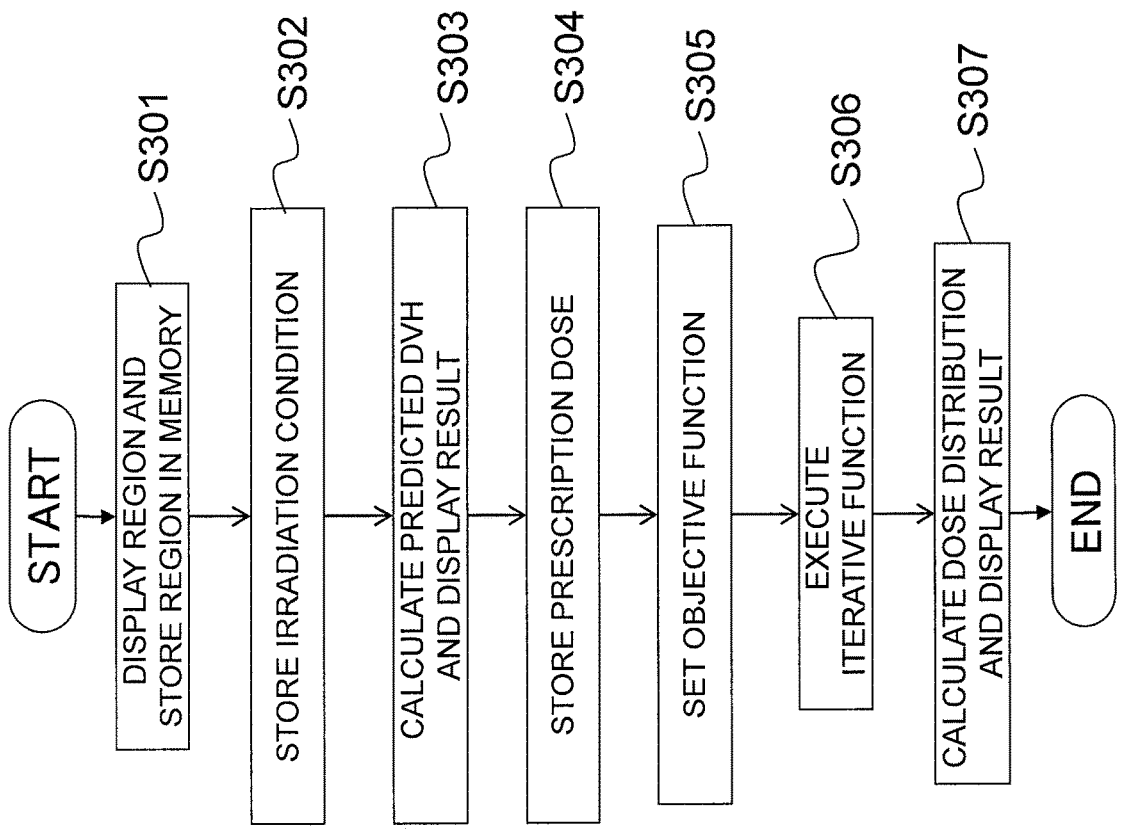
FIG. 6 is a diagram illustrating the processing operation of the radiation treatment planning system of the present invention.
Figure 7:
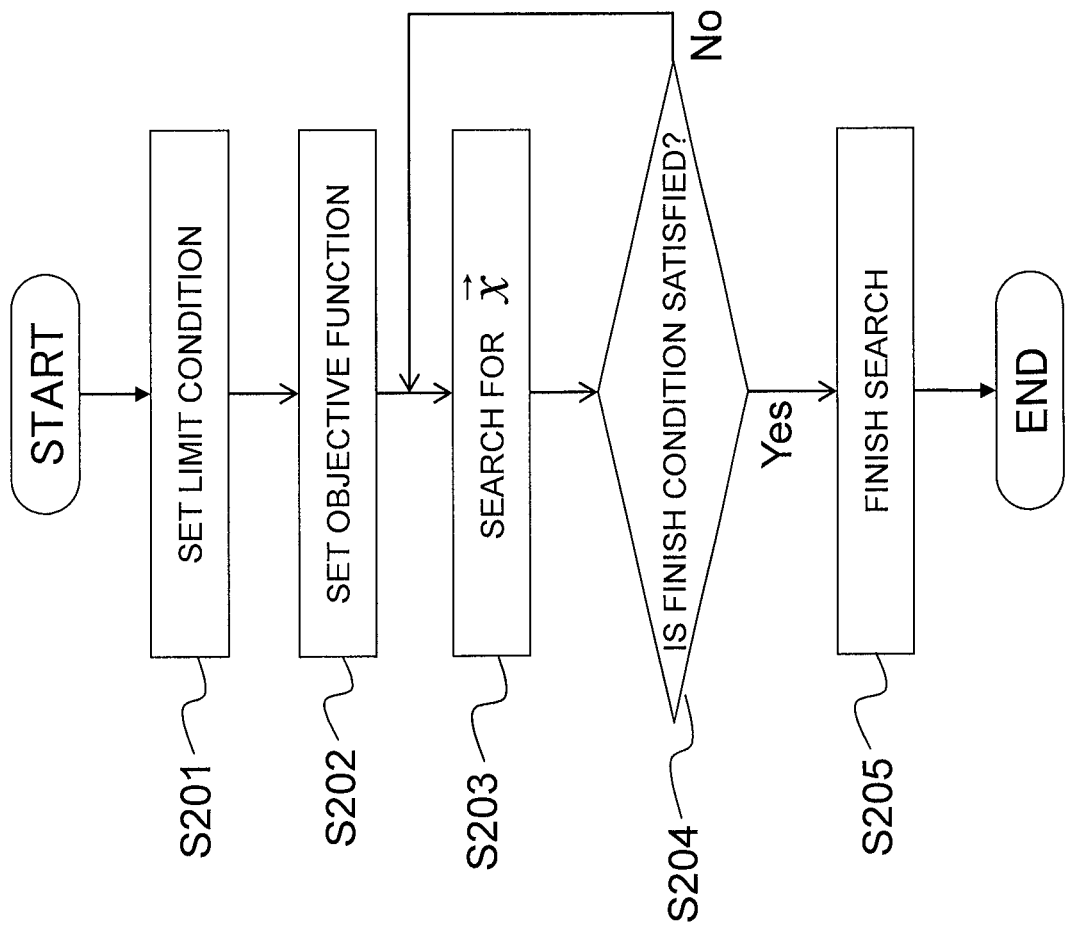
FIG. 7 is a diagram illustrating a flow of a method for searching for an irradiation amount by a spot scanning method.

FIG. 1 is a diagram illustrating a whole configuration of a particle beam therapy system in which a particle beam irradiation apparatus and the radiation treatment planning system are connected to each other. FIG. 2 is a diagram illustrating a screen such as a target region on a CT screen, and FIG. 3 is a diagram for describing a method for calculating an OV and a predicted DVH. FIG. 4 is a diagram illustrating a state where the predicted DVH and the calculated DVH are displayed by being overlapped. FIG. 5 is a diagram representing a flow of a processing operation for making radiation treatment planning, FIG. 6 is a diagram illustrating the operation which is performed by the radiation treatment planning system according to the embodiment of the present invention, and FIG. 7 is a diagram illustrating a flow of a method for searching for an irradiation amount to an irradiated body by a spot scanning method.

First, the scanning irradiation will be described. In the scanning irradiation, there are a spot scanning method and a raster method. The spot scanning method is a method in which a target is divided into a plurality of points (spots), after irradiating a certain spot with a beam of a specified amount, the beam is stopped once, and after moving to a next spot to be irradiated, the irradiation is started again, thereby, the irradiation with radiation is sequentially performed. The raster method is a method in which irradiation with the radiation is sequentially performed without stopping the beam while an irradiation point is moved. The present invention may be applied to the raster method.

In FIG. 1, a radiation treatment system 410 includes a radiation treatment planning system 400 for irradiating the target with the radiation and preparing the treatment plan, and a particle beam irradiation apparatus 406 that irradiates a target region 501 (see FIG. 2) with the radiation based on the treatment planning which is prepared by the radiation treatment planning system 400.

As illustrated in FIG. 1, the radiation treatment planning system 400 includes a display device 401, an input device 402, an arithmetic processing device 403, a memory 404, and a data server (database) 405. The data server 405 is also connected to the particle beam irradiation apparatus 406.

The data server 405 is a storage medium that stores past treatment planning data. In particular, the data server 405 stores information on an average dose $D_j$ and a standard deviation $\sigma_j$ of the dose in an OV which is overlapped with an organ-at-risk region 502 by increasing a volume of the target region 501.

The display device 401 is a device for providing the information or the like to an operator, when various information which is necessary at the time of preparing the treatment plan, or execution, setting change, or finish of various processing is input. In the embodiment, for example, a predicted target DVH 702 and a predicted organ-at-risk DVH 712 (see FIG. 4) which are calculated by a predicted DVH calculation portion 4034 described later, and a calculated target DVH 701 and a calculated organ-at-risk DVH 711 (see FIG. 4) which are calculated by an optimization calculation portion 4032 described later are displayed by being overlapped.

The input device 402 is a device for inputting various information, or execution, setting change or finish of various processing by the operator, at the time of preparing the treatment plan, and is, for example, a keyboard or a mouse. By using the input device 402, the operator designates a position of an irradiated body such as the target region 501 or the organ-at-risk region 502, from a CT image for the treatment planning which is prepared in advance.

The memory 404 is a storage device that temporarily stores the information used at the time of performing various arithmetic processing in the arithmetic processing device 403 described later.

The arithmetic processing device 403 includes a controller 4031, the optimization calculation portion 4032, a dose calculation portion 4033, and the predicted DVH calculation portion 4034. Irradiation conditions, dose distribution and the like which are optimized by the arithmetic processing device 403 are stored in the data server 405, and the irradiation conditions are further transferred to the particle beam irradiation apparatus 406.

The controller 4031 performs a control of the arithmetic processing in the optimization calculation portion 4032, the dose calculation portion 4033, and the predicted DVH calculation portion 4034 in the arithmetic processing device 403.

The optimization calculation portion 4032 will be described later in detail, but defines an objective function, and performs the calculation thereof. The optimization calculation portion 4032 calculates the calculated target DVH 701 of the target region 501, and the calculated organ-at-risk DVH 711 of the organ-at-risk region 502, from the dose with respect to the calculated target region 501.

The dose calculation portion 4033 performs the calculation of the dose distribution, by calculating the irradiation amount per spot which is calculated by the optimization calculation portion 4032.

The predicted DVH calculation portion 4034 calculates a region (Overlap Volume (OV), $OV_1$, $OV_2$, $OV_3$, . . . , in FIG. 3) where the organ-at-risk region 502 and the target region 501 are overlapped by anisotropically changing the target region 501 in the CT image for the treatment planning which is designated by the input device 402. Based on the calculated OV and the past treatment planning data which is stored in the data server 405, a predicted DVH (predicted target DVH 702) of the target and a predicted DVH (predicted organ-at-risk DVH 712) of the organ-at-risk are calculated.

The predicted DVH calculation portion 4034 will be described in detail later, but at the time of calculating the predicted DVH, the predicted DVH calculation portion 4034 anisotropically changes, specifically, anisotropically enlarges the target region 501, based on the information on an irradiation direction of the radiation and a depth from a body contour (body surface) 503 (see FIG. 2) to the target region 501. At the time of being anisotropically enlarged, an enlargement amount on a side which is close to the body contour 503 in comparison with the target region 501 is made larger than an enlargement amount on a side which is distant to the body contour 503 in comparison with the target region 501.

The particle beam irradiation apparatus 406 is an apparatus for irradiating the target region 501 with the radiation, and includes an injection portion 4061 that performs initial acceleration by generating a proton beam, an acceleration portion 4062 that accelerates the proton beam up to predetermined energy, and an irradiation controller 4063 that forms the proton beam, and controls the irradiation. The particle beam with which is irradiated by the particle beam irradiation apparatus 406 is not limited to the proton, and may be a particle of which mass is larger than the proton, for example, a carbon ion or the like.

Next, details of the preparation processing of the treatment planning of the embodiment using the radiation treatment planning system 400 will be described hereinafter, with reference to FIGS. 5 to 7.

First, the operator inputs the region (the target region 501, the organ-at-risk region 502, and the body contour (body surface) 503) to be designated per slice of the CT image of the irradiated body, onto a region input screen the display device 401 of the radiation treatment planning system 400, by using the input device 402. If the input is finished in each slice, the operator registers the input region. In a case where there is another region which is necessary for evaluation or control, such that the organ-at-risk to prevent the irradiation dose to the irradiated body as much as possible exits in the vicinity of the target region, the operator registers the positions of the organs-at-risk in the same manner. By performing the registration, the region which is input by the operator is stored in the memory 404 as three-dimensional position information. FIG. 2 illustrates the state where the operator inputs the target region 501, the organ-at-risk region 502, and the body contour 503 onto a certain slice of the CT image in the display device 401, as an example. The operator performs registration instruction operations of the respective input regions 501, 502, and 503 to the radiation treatment planning system 400, and performs the registration thereof (step S101).

As a result, the position of the input target region 501 or the input organ-at-risk region 502 is registered in the radiation treatment planning system 400, and is stored in the memory 404 (FIG. 6, step S301).

Subsequently, the operator determines the irradiation condition with respect to the registered target region (FIG. 5, step S102). That is, the number of irradiation gates or the irradiation direction is set, based on the positions of the target region and the organ-at-risk. The set irradiation condition is stored in the memory 404 (FIG. 6, step S302). In the irradiation conditions which are determined in step S102, all thereof is not determined by the operator, but may be automatically determined by the system. In a case where the scanning irradiation method is adopted in the particle beam therapy as the embodiment, a large number of spot positions be necessarily determined, and the irradiation beam energy to each spot or an irradiation interval can be an item to be set.

Subsequently, the radiation treatment planning system 400 calculates the predicted DVH by the predicted DVH calculation portion 4034 of the arithmetic processing device 403, and displays a calculation result on the display device 401 (FIG. 6, step S303). Hereinafter, the calculation process of the predicted DVH will be described by using FIG. 3.

First, the predicted DVH calculation portion 4034 increases the volume of the target region 501 in an irradiated body image, and calculates the OV with the organ-at-risk region 502. In order to calculate an increase direction of the target region 501, the predicted DVH calculation portion 4034 obtains a normal vector $r_i$ (i=1 to N) Of a target surface. N indicates the number of normal vectors $r_i$ of the target surface. A point $P_i$ is an intersection point of $r_i$ with the target, and is uniformly distributed on the target surface. A magnitude of the normal vector $r_i$ is represented by $A_1$, and is the same in all surfaces. A case where approximately $A_1$=1 to 10 mm is considered to be valid in the calculation of the OV, but the case can be suitably modified in accordance with protocol or the like of each facility.

Next, the predicted DVH calculation portion 4034 decomposes the normal vector $r_i$ into two components of a component $r_{i1}$ which is parallel to a beam irradiation direction $B_1$ and a component rig which is vertical to $B_1$, and the magnitude of each component is adjusted based on Expressions (1) and (2).

$$r_{i1}' = C_1 \times r_{i1} \quad (1)$$

$$r_{i2}' = C_2 \times r_{i2} \quad (2)$$

Here, z is a depth from the body surface to the point $P_i$ in the beam irradiation direction $B_1$, and is to be $C_2(z) > 0$. $C_2(z)$ indicates the enlargement amount of the target region 501 in a lateral direction, and is changed depending on the depth z. For example, in the vicinity of the depth of 30 cm or in a shallow portion of a range of 10 cm or less, the enlargement of the spot size becomes a relatively large value.

$C_1$ in Expression (1) is represented as Expression (3).

$$C_1 = A_2(r_{i1} \cdot B_1 \geq 0) \quad (3)$$
$$= A_3(r_{i1} \cdot B_1 < 0)$$

Here, it is made to be $A_3 > A_2 > 0$. $A_2$ indicates the enlargement amount of the target region 501 on a distal side. Since the particle beam has the range, and the dose is hardly dropped after the Bragg peak, $A_2$ becomes a relatively small value. On the other hand, $A_3$ indicates the target enlargement amount on a proximal side, and obtains a relatively large value from a shape of the Bragg curve including the low dose region in the vicinity of a water surface.

If the normal vector after the adjustment is performed by Expression (1) to Expression (3) is referred to as $r_i'$, a target region 601 after the enlargement is a region which is surrounded by the following points $P_i'$.

$$P_i' = r_i' + P_i \quad (4)$$

The anisotropic enlargement of the target region 501 is realized by Expression (1) to Expression (3) in the embodiment, but so long as being the enlargement method having a correlation with the dose distribution of the particle beam, effects which are equivalent to the embodiment are obtained.

If it is made to be "$A_3 = A_2 = C_2$ (z)=constant" in Expression (1) to Expression (3) described above, the processing becomes the processing which is equivalent to the enlargement of the target region as described in NPL 1.

Next, as illustrated in FIG. 3, the predicted DVH calculation portion 4034 further enlarges the target region 601 which is enlarged in accordance with the above procedure, and further calculates the region which is overlapped with the organ-at-risk region 502, that is, the OV. Here, a difference between the OV of the target and the organ-at-risk receiving the j−1-th enlargement and the OV of the target and the organ-at-risk receiving the j-th enlargement is referred to as $OV_j$. The volume of the $OV_j$ is referred to as $dV_j$.

$A_2$, $A_3$, and $C_2(z)$ which are illustrated in Expression (1) to Expression (3) are fixed values in the embodiment, but may be changed in accordance with the number of times of enlargement j, depending on the actual data.

Next, the predicted DVH calculation portion 4034 accesses the information on the average dose $D_j$ and the standard deviation $\sigma_j$ of the dose in the $OV_j$ that is obtained from a treatment data group which is stored in the data server 405 and is carried out in the past, and calculates the volume of a dose histogram of the organ-at-risk region 502 and the volume $dV_j$ in accordance with Expression (5). Here, m indicates the number of times of enlargement until the organ-at-risk is fully included in the target.

$$V(x) = \sum_{j=0}^{m} \frac{dV_j}{\sqrt{2\pi\sigma_j^2}} \exp\left(-\frac{(x-D_j)^2}{2\sigma_j^2}\right) \quad (5)$$

Finally, the predicted DVH calculation portion 4034 integrates and displays the result of Expression (5) into the predicted DVH, and displays the result thereof on the display device 401.

In the embodiment, the dose histogram in the $OV_j$ is modeled by Gaussian distribution, but the distribution shape may be changed depending on the actual data (Cauchy distribution, Landau distribution, or the like). It is possible to change the distribution shape per the number of times of enlargement j.

Next, the operator sets the prescription dose to each registered region (target region 501 and organ-at-risk region 502) (step S103).

If the set prescription dose is in the target region 501, there are many cases where the minimum value or the maximum value of the dose to be received within the region is input, but here, a dose value to be irradiated to the target region 501 is designated by one. On the other hand, there are many cases where a tolerance dose is set with respect to the organ-at-risk region 502. Based on the shape of the predicted DVH which is displayed on the display device 401, the operator designates the tolerance dose to the organ-at-risk region 502. In addition thereto, the predicted DVH calculation portion 4034 may automatically set the tolerance dose of the organ-at-risk, based on the shape of the predicted DVH. In such a case, the operator once confirms the tolerance dose which is automatically input, and adjusts the tolerance dose if necessary, thereby, designates the value to the radiation treatment planning system 400.

The irradiation direction and the prescription dose which are set as described above are stored in the memory 404 (FIG. 6, step S304).

Next, the radiation treatment planning system 400 defines the objective function that is obtained by quantifying the deviation from the prescription dose (FIG. 6, step S305), and performs an iterative function (FIG. 6, step S306). The objective function is minimized due to the iterative function in step S306, thereby, the remaining parameter relating to the irradiation condition such as the irradiation amount per spot, is calculated.

In step S306, the dose calculation portion 4033 of the arithmetic processing device 403 performs the dose distribution calculation, and stores the data of the result thereof in the memory 404. Per iterative function, the dose distribution result data which is stored in the memory 404 is read out, and the parameter is calculated by using the objective function. The iterative function, and the read-out of the data from the memory 404 are performed by a command from the controller 4031. The definition and the calculation of the objective function are executed by the optimization calculation portion 4032 of the arithmetic processing device 403. In a case where the spot scanning irradiation method is adopted as described above, the irradiation amount (spot irradiation amount) to each spot is included in the parameters which are calculated by using the objective function.

Here, an example of a method for searching for the parameter using the objective function, will be described with reference to FIG. 7.

In the method for searching for the parameter using the objective function, first, the operator first sets a limit condition from the information on the prescription dose or the organ-at-risk, by using the input device 402 (FIG. 7, step S201).

Subsequently, the radiation treatment planning system 400 respectively sets m points and n points for calculating the dose in each of the target region 501 and the organ-at-risk region 502, and prepares the objective function based on the limit condition (FIG. 7, step S202).

If a vector having the dose values at m points in the target region 501 as an element is referred to as $d^{(1)}$, the relationship between $d^{(1)}$ and a vector x having the spot irradiation amount as an element is represented by Expression (6).

$$d^{(1)}=Ax \tag{6}$$

In Expression (6), a matrix A represents the dose (dose matrix) that is applied to a calculation point in the target region from the beam with which each spot is irradiated, and is calculated based on the irradiation direction and the internal information by the CT image.

Similarly, if a vector having the dose values at n points in the organ-at-risk region 502 as an element is referred to as $d^{(2)}$, it is possible to represent $d^{(2)}=Bx$ in the same manner as Expression (6). B is a matrix that is the same as the matrix A, and is the dose (dose matrix) that is applied to the calculation point in the organ-at-risk from the beam with which each spot is irradiated.

In step S201, in a case where a dose value p which becomes the target with respect to m points corresponding to the target region 501, and a tolerance dose value l with respect to n points corresponding to the organ-at-risk region 502 are set as a limit condition, an objective function F(x) is set as Expression (7).

$$F(x) = \sum_{i=1}^{m} w_i^{(1)}(d_i^{(1)} - p)^2 + \sum_{i=1}^{n} w_i^{(2)}(d_i^{(2)} - l)^2 \theta(d_i^{(2)} - l) \tag{7}$$

In Expression (7), $W_i^{(1)}$ and $W_i^{(2)}$ are weights corresponding to the respective points, and are values which are input along with the prescription dose by the operator.

A first term of Expression (7) is an equivalent portion to the target region, and the closer the dose value at m points is to the prescription dose value p which is set as a target, the smaller the objective function F(x) becomes. A second term of Expression (7) is a term relating to the organ-at-risk, and may be any so long as being the dose which does not exceed the tolerance dose l. $\theta(d_i^{(2)}-l)$ of Expression (7) is a step function, and becomes 0 in a case of $d_i^{(2)}<l$, and becomes 1 in other cases.

After the objective function F(x) of Expression (7) is generated, the radiation treatment planning system 400 repeats the iterative function until a finish condition of the iterative function is satisfied, thereby, searches for $X^{\rightarrow}$ in which the objective function F(x) becomes the smallest (FIG. 7, step S203).

Next, it is determined whether or not the finish condition of the iterative function is satisfied (FIG. 7, step S204). As described above, an index such as the calculation time, the number of time of calculations, or the change amount of the objective function is set into the finish condition.

When it is determined that the finish condition is satisfied, the processing proceeds to step S205, and the radiation treatment planning system 400 finishes the search by finishing the iterative function (FIG. 7, step S205). When it is determined that the finish condition is not satisfied, the processing returns to step S203, and the iterative function is executed again.

In the operation flow of FIG. 6, the radiation treatment planning system 400 calculates the dose distribution based on the spot irradiation amount which is finally obtained as a result of the iterative function, and displays the result thereof on the display device 401 (FIG. 6, step S307).

The above operation is equivalent to the irradiation amount search in step S104 in FIG. 5.

On the display device 401, the DVH (the calculated target DVH 701, the calculated organ-at-risk DVH 711 in FIG. 4) which is finally obtained as a result of the iterative function, and the predicted DHV (the predicted target DVH 702, the predicted organ-at-risk DVH 712) are displayed by being overlapped.

In FIG. 4, the target DVH (calculated target DVH 701) of the calculation result is represented by a solid line, the DVH (predicted target DVH 702) of the predicted target is represented by a dotted line, the organ-at-risk DVH (calculated organ-at-risk DVH 711) of the calculation result is represented by a broken line, and the DVH (predicted organ-at-risk DVH 712) of the predicted organ-at-risk is represented by a dashed line.

As illustrated in FIG. 4, it is understood that the applied dose (calculated target DVH 701) to the target has portions of the low dose and the high dose in comparison with the predicted target DVH 702 which is predicted. On the other hand, it is understood that the dose allowance (calculated organ-at-risk DVH 711) is generally smaller than the prediction (predicted organ-at-risk DVH 712) with respect to the organ-at-risk. In this case, it is possible to tolerate the increase of the applied dose to the organ-at-risk, within a scope of the applied dose which is tolerated to the organ-at-risk, thereby, it possible to improve the dose distribution to the target, and it is possible to easily perform the determination.

The operator determines whether or not the dose distribution obtained as a result of the iterative function satisfies the condition designated as a prescription dose with reference to the display as illustrated in FIG. 4 (step S105). When it is determined that the determined condition is satisfied, the condition is fixed, and is stored in the memory 404 by the instruction of the operator, and the irradiation condition is output to the data server 405 (FIG. 5, step S106), thereby, the preparation of the treatment planning is completed.

On the other hand, in step S105, in a case where the operator determines that the condition is not satisfied, for example, in a case where a region that is largely different from the prescription dose is confirmed, the processing returns to step S102, the irradiation condition and the prescription dose are changed, and the planning is remade.

However, in the embodiment, the prescription dose is input as a valid numerical value based on the past data. Accordingly, even in a case where there is a need to remake the planning, it is possible to deal with small correction such as the change of the weight of the objective function in most cases.

Thereafter, in the data server 405, the dose vector $d_i$ (the number of elements is the number of voxels which are included in the $OV_j$) in the $OV_j$ is extracted from the sent dose distribution and the irradiated body image, and is added to the past treatment planning data group, and the information on the average dose $D_j$ and the standard deviation $\sigma_j$ of the dose in the $OV_j$ is updated. At this case, in order to improve prediction accuracy of the DVH, useful is a method in which the past treatment planning data group is classified according thereto per treatment site or the like, and the parameter (the average dose $D_j$, the standard deviation $\sigma_j$ of the dose, in the embodiment) which is necessary for the calculation of the predicted DVH is store, and is updated.

Next effects of the present embodiment will be described.

The radiation treatment system 410 of the embodiment described above, includes the particle beam irradiation apparatus 406 that irradiates the target region 501 with the radiation, and the radiation treatment planning system 400. The radiation treatment planning system 400 includes the data server 405 that stores the past treatment planning data, the display device 401 that displays the DVH, and the predicted DVH calculation portion 4034 that calculates the predicted target DVH 702 and the predicted organ-at-risk DVH 712, and the predicted DVH calculation portion 4034 calculates the $OV_1$, the $OV_2$, the $OV_3$, . . . between the organ-at-risk region 502 and the target region 501 by anisotropically changing the target region 501 in the image where the target region 501 and the organ-at-risk region 502 are imaged, and calculates the predicted target DVH 702, and the predicted organ-at-risk DVH 712 based on the calculated $OV_1$, $OV_2$, $OV_3$, . . . , and the past treatment planning data which is stored in the data server 405, and the display device 401 displays the predicted target DVH 702, and the predicted organ-at-risk DVH 712 which are calculated by the predicted DVH calculation portion 4034.

With such a configuration, it is possible to display the predicted DVHs 711 and 712 as a target value of the treatment planning on the display device 401. Therefore, it is possible to instantly determine whether or not to need to perform the treatment planning again with decision making by the operator, that is, by changing the parameter. Since the OV is calculated by anisotropically changing the target region 501, and the displayed predicted DVHs 711 and 712 are calculated based on the calculated OV and the past treatment planning data which is stored in the data server 405, by existence of the Bragg peak due to physical properties of the particle beam and a difference of a spot diameter per energy, the dose distribution has the anisotropic spread depending on an irradiation angle of the beam, the depth from the body surface to the target, or the like, and even in the scanning irradiation method, it is possible to reflect the anisotropic spread. Accordingly, it is possible to perform support of the decision making by the operator with high accuracy, and it is possible to shorten the time which is necessary for preparing the treatment plan.

The predicted DVH calculation portion 4034 anisotropically changes the target region 501 based on the information on the irradiation direction of the radiation, and the depth from the body contour (body surface) 503 to the target region 501, and in particular, since the predicted DVH calculation portion 4034 makes the change amount of the anisotropic change on the side which is close to the body contour 503 in comparison with the target region 501 larger than the change amount of the anisotropic change on the side which is distant to the body contour 503 in comparison with the target region 501, it is possible to calculate the predicted DVH more accurately by reflecting the anisotropic spread, and it is possible to further enhance the accuracy of the support of the decision making by the operator.

The optimization calculation portion 4032 that calculates the calculated target DVH 701 and the calculated organ-at-risk DVH 711 of the target region 501 and the organ-at-risk region 502 from the dose with respect to the target region 501, is further included, and the display device 401 displays the predicted target DVH 702, the predicted organ-at-risk DVH 712, and the calculated target DVH 701 and the calculated organ-at-risk DVH 711 which are calculated by the optimization calculation portion 4032 by being overlapped, thereby, the predicted DVHs are displayed as a target value of the treatment plan. Therefore, it is possible to instantly determine whether or not to need to perform the treatment planning again with the decision making by the operator, that is, by changing the parameter. Accordingly, in the radiation treatment of the scanning irradiation method, it is possible to further achieve time shortening and labor saving of the treatment planning making.

In the positional relationship between the target region 501 and the organ-at-risk region 502, in many cases, since the calculation of the OV is performed by anisotropically enlarging the target region 501, the predicted DVH calculation portion 4034 may correspond to many cases by anisotropically enlarging the target region 501.

OTHERS

The present invention is not limited to the embodiments described above, and may be variously modified or applied. The embodiments described above are described in detail in order to easily understand and describe the present invention, and are not necessarily limited to the embodiments including all configurations described.

For example, a case of anisotropic enlargement is described, but the present invention can be applied to a case of anisotropic reduction. For example, there is a case where a margin of the target region is made sufficient in consideration of an irradiation error of the particle beam in advance, a case where the distance between the target region and the organ-at-risk is short, or a case where the target region and the organ-at-risk are overlapped in advance. In such a case, the predicted DVH calculation portion 4034 decreases the volume of the target region in the irradiated body image, and calculates the OV with the organ-at-risk region. At this time, a case of decrease may basically be the same as a case of enlargement described above, and a decrease amount on the side which is close to the body contour in comparison with the target region is made larger than a decrease amount on the side which is distant to the body contour in comparison with the target region, thereby, the target region is anisotropically decreased. In the same manner, it is possible to the time shortening and the labor saving for preparing the treatment plan, even by such a method.

REFERENCE SIGNS LIST

400: RADIATION TREATMENT PLANNING SYSTEM
401: DISPLAY DEVICE
402: INPUT DEVICE
403: ARITHMETIC PROCESSING DEVICE
4031: CONTROLLER
4032: OPTIMIZATION CALCULATION PORTION
4033: DOSE CALCULATION PORTION
4034: PREDICTED DVH CALCULATION PORTION
404: MEMORY
405: DATA SERVER (DATABASE)
406: PARTICLE BEAM IRRADIATION APPARATUS
4061: INJECTION PORTION
4062: ACCELERATION PORTION
4063: IRRADIATION CONTROLLER
410: RADIATION TREATMENT SYSTEM
501: TARGET REGION
502: ORGAN-AT-RISK REGION
503: BODY CONTOUR (BODY SURFACE)
601: ENLARGED TARGET REGION

The invention claimed is:

1. A radiation treatment planning system for preparing a radiation treatment plan, the system comprising:
   a processor connected to memory;
   a database connected to the processor that stores past treatment planning data;
   a display device that displays a dose volume histogram (DVH); and
   wherein the memory stores instructions that when executed by the processor configures the processor to:
   calculate an overlap volume (OV) between an organ-at-risk region and a target region by anisotropically changing the target region in an image of an irradiated body,
   calculate a predicted DVH based on the calculated OV, and the past treatment planning data which is stored in the database, and
   display the predicted DVH on the display device.

2. The radiation treatment planning system according to claim 1, wherein the processor is further configured to anisotropically change the target region based on information on an irradiation direction and a depth which is from a body surface to the target region.

3. The radiation treatment planning system according to claim 2,
   wherein the processor is further configured to make a change amount of an anisotropic change on a side which is close to the body surface in comparison with the target region larger than a change amount of an anisotropic change on a side which is distant to the body surface in comparison with the target region.

4. The radiation treatment planning system according to claim 1, wherein the processor is further configured to calculate DVHs of the target region and the organ-at-risk region from a dose with respect to the target region, and
   display the predicted DVH, and the DVHs of the target region and the organ-at-risk region in an overlapping manner.

5. The radiation treatment planning system according to claim 1,
   wherein the processor is further configured to anisotropically enlarge the target region.

6. The radiation treatment planning system according to claim 1, wherein the radiation treatment plan divides the target region into a plurality of small regions, and
   wherein irradiation is carried out according to the radiation treatment plan by sequentially irradiating the plurality of small regions with radiation.

7. The radiation treatment planning system according to claim 1,
   wherein irradiation is carried out according to the radiation treatment plan by particle beam that is configured with proton ions, or particle ions of which mass is larger than a proton.

8. A radiation treatment system comprising:
   an irradiation apparatus that irradiates a target region with radiation; and
   the radiation treatment planning system according to claim 1,
   wherein irradiation performed by the irradiation apparatus is carried out according to the radiation treatment plan prepared by the radiation treatment planning system.

* * * * *